US005618539A

United States Patent [19]

Dorval et al.

[11] Patent Number: 5,618,539

[45] Date of Patent: Apr. 8, 1997

[54] STABILIZED VACCINE COMPOSITIONS

[75] Inventors: Brent Dorval, Leominster; Marie Chow, Brookline; Alexander Klibanov, Newton, all of Mass.

[73] Assignee: Massachusetts Institute of Technology, Cambridge, Mass.

[21] Appl. No.: 314,571

[22] Filed: Sep. 29, 1994

Related U.S. Application Data

[63] Continuation of Ser. No. 393,996, Aug. 15, 1989, abandoned.

[51] Int. Cl.[6] .......... A61K 39/13

[52] U.S. Cl. .......... 424/217.1

[58] Field of Search .......... 424/217.1

[56] References Cited

U.S. PATENT DOCUMENTS

| | | | |
|---|---|---|---|
| 3,097,142 | 7/1963 | Schuchardt et al. | 167/78 |
| 3,097,143 | 7/1963 | Schuchardt et al. | 167/78 |
| 3,128,229 | 4/1964 | Melnick et al. | 424/361 |
| 4,337,242 | 6/1982 | Markus et al. | 424/89 |
| 4,338,335 | 7/1982 | McAleer et al. | 424/361 |

FOREIGN PATENT DOCUMENTS

| | | |
|---|---|---|
| 0065905 | 12/1982 | European Pat. Off. . |
| 45-18877 | 6/1970 | Japan . |
| 1564998 | 4/1980 | United Kingdom . |

OTHER PUBLICATIONS

Savithri et al. J. Gen. Virol. 68(6) 1533–42 1987.

Davis et al. *Microbiology* Harper and Row ed. 3rd. Ed. 1980. pp. 1107–1109.

Fundamental Virology Raven Press 1991.

Dorval, B.L., et al., "Lysine and Other Diamines Dramatically Stabilize Poliovirus against Thermoinactivation", *Biotechnology and Bioengineering* 35:1051–1054 (1990).

"Physicians Desk Reference", 1986, pp. 1023, 1164 & 1165.

*Primary Examiner*—Toni R. Scheiner

*Attorney, Agent, or Firm*—Hamilton, Brook, Smith & Reynolds, P.C.

[57] ABSTRACT

Non-lyophilized vaccine compositions which contain a poliovirus and, as stabilizer, a compound containing at least two amino or imine groups. The stabilizers include polyimines such as the amino acid lysine or ethylenediamine and polyimines such as poly(ethylenimine).

32 Claims, 2 Drawing Sheets

STABILIZED VACCINE COMPOSITIONS

RELATED APPLICATION

This application is a continuation of application Ser. No. 07/393,996 filed on Aug. 15, 1989, now abandoned, which is incorporated herein by reference in its entirety.

GOVERNMENT SUPPORT

The work leading to this invention was supported by a grant from the National Institutes of Health. The U.S. Government has certain rights to this invention.

BACKGROUND OF THE INVENTION

The trivalent oral polio vaccine (Sabin) is a live-attenuated virus vaccine. It is heat-labile and hence must be stored frozen and used soon after thawing to insure effective immunization against poliomyelitis. Although 1 molar magnesium chloride is an effective stabilizer for the Sabin vaccine, inactivation will still occur if the vaccine thaws during transport or storage. Because of the shortage of adequate refrigeration facilities in underdeveloped and tropical regions, where poliovirus is endemic, the vaccine often cannot be stored frozen and as a consequence the vaccine becomes inactivated. This leads to under-immunization of the populations which are most at risk. Thus, eradication of poliomyelitis depends on the ability to assure cold storage and rapid distribution of poliovirus vaccine. Vaccine formulations with improved stability would circumvent this problem.

SUMMARY OF THE INVENTION

This invention pertains to stabilized viral vaccines, particularly live viral vaccines for poliomyelitis, comprising an aqueous solution of a live virus and a stabilizing amount of a compound containing at least two amino or imine groups, such as basic amino acids (e.g. lysine). These compounds are safe, relatively inexpensive and can be easily added to viral vaccine preparations. The polyamino or imine compound improves the heat stability of the virus in standard tests for viral stability over that of the currently available stabilizer magnesium chloride. This provides more stable live viral vaccine compositions for worldwide distribution and use.

DETAILED DESCRIPTION OF THE INVENTION

Figure 1:
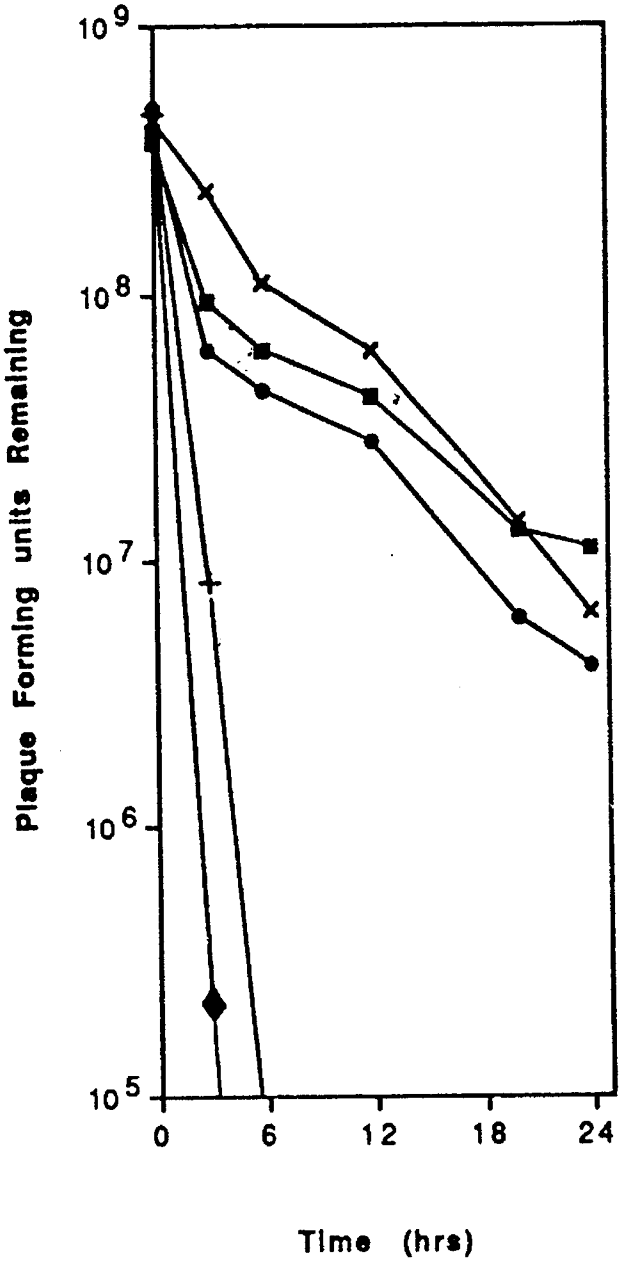
FIG. 1 shows stabilization of poliovirus (serotype 1, Mahoney strain) against heat inactivation by 1M amino acids or $MgCl_2$. Poliovirus, $4\times10^8$ plaque forming units (PFU, approximately 80 viral particles), was added to 1 ml of 5 mM phosphate buffer, pH 7.0, containing 1M each of L-lysine (■), L-arginine (×), glycine (♦), L-alanine (+) or $MgCl_2$ (●). The resultant solution was placed in 1.4 ml Eppendorf tubes, sealed and submerged in a water bath at 50° C. Aliquots were removed periodically, diluted with with 5 mM phosphate buffer containing 150 mM NaCl, pH 7.0 (PBS), and the titer of infectious poliovirus was followed by plaque assay on HeLa cells.

The vaccine compositions of this invention comprise a virus and a compound, containing at least two amino or imine groups, in an amount sufficient to stabilize the virus. The amino or imine compound enhances the stability of the virus against heat inactivation. For example, in standard tests for virus stability at 50° C., the stability of the virus is enhanced at least 10–20 fold by the amino acid lysine. The vaccine compositions are produced by adding the virus and a stabilizing amount of the amino or imine containing compound into a physiologically acceptable aqueous solution.

The amino or imine containing compound can be any non-toxic compound containing at least two amino or imine groups. Preferably, the compounds comprise at least two primary or secondary amino or imine groups separated by a spacer moiety. The size or constituency of the spacer moiety does not appear to be critical. Typically, the spacer moiety will consist of a substituted or unsubstituted, linear chain of carbon atoms (heteroatoms such as nitrogen may be included in the chain) ranging from 1 to about 10, preferably from 1 to about 6 atoms. Preferred compounds are the amino acids lysine and arginine or salts (e.g., chloride or acetate) thereof. Some examples of other useful compounds include diaminoethane, 1,3-diaminopropane, 1,4-diaminobutane, and 1,5-diaminopentane. Other stabilizers include compounds which have a nitrogen carrying spacer moiety such as spermidine. In addition, polyimines such as poly(ethylenimine) can be used. Mixtures of amino or imine containing compounds can also be used.

The stabilizer compound is used in an amount effective to stabilize the virus. Generally, the concentration of the amino compound is 1–2 molar.

The virus can be any virus or mixture of viruses. Generally, the virus will be attenuated. For vaccines against poliomyelitis, the vaccine compositions can contain any or all of the various types of poliovirus. The preferred vaccines are the trivalent Sabin vaccines which contain types I, II and III of poliovirus.

The vaccine compositions will typically be formulated at a pH ranging from about 6 to 8. Magnesium chloride, preferably 1 molar, can also be added to the compositions.

Other immunogens such as diphtheria toxoid, tetanus toxoid and inactivated pertussis cells can combine with the viral components of the compositions. In addition, the compositions can contain adjuvants which do not interfere with the activity of the stabilizing compound.

The invention is illustrated further by the following exemplification.

EXEMPLIFICATION

Methods and Materials

Poliovirus (serotype 1, Mahoney strain) (PV1M) was grown in HeLa cells, purified on cesium chloride gradients and dialyzed against PBS, pH 7.2. Viral stocks contained approximately $4\times10^{11}$ PFU/ml and were stored at 4° C.

Approximately $4\times10^8$ PFU were added to 1 ml of 5 mM phosphate buffer, pH 7.0, alone or containing 1 M L-lysine, D-lysine, L-arginine, glycine, L-alanine, N-α-acetyl-L- lysine, N-ε-acetyl-L-lysine, L-lysine methyl ester, ethylenediamine, 1,5-diaminopentane, ethylamine, poly(ethylenimine), spermidine or $MgCl_2$. The pH of each solution was adjusted to 7.0 with HCl prior to the addition of poliovirus. The resulting solutions were placed in 1.4 ml Eppendorf tubes, sealed and submerged in a water bath at 50° C. Aliquots (10–100 μl) were removed periodically, diluted with PBS and the titer of infectious poliovirus was followed by plaque assay on HeLa cells.

Results

In the first experiment we tested the ability of 1M concentrations of L-amino acids and $MgCl_2$, pH 7.0, to stabilize PV1M against heat inactivation at 50° C. FIG. 1 demonstrates that lysine and arginine stabilize PV1M 2 to 4 times better than $MgCl_2$ at all time points, whereas, L-alanine and glycine provide 10 to 10,000 times less stabilization than $MgCl_2$ during the same period. In controls, which contained 5 mM phosphate buffer alone at pH 7.0, more than eight orders of magnitude of viral infectivity were lost after 3 hours.

Figure 2:
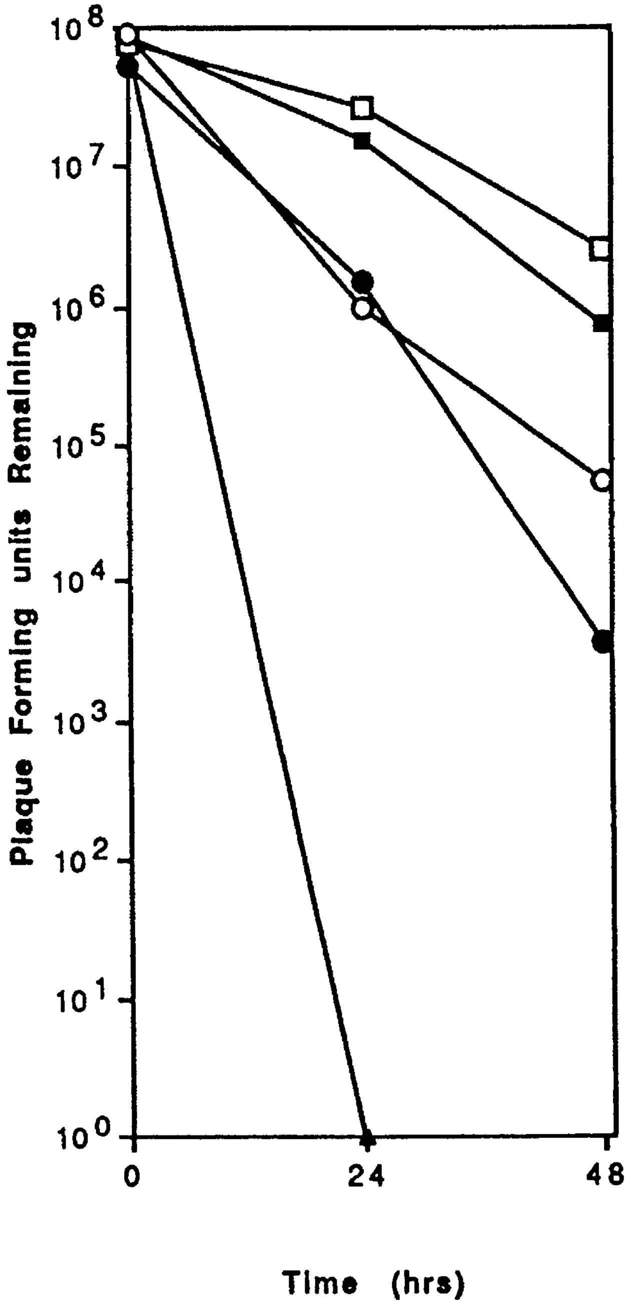
FIG. 2 shows stabilization of poliovirus (serotype 1, Mahoney strain) against heat inactivation by 1 or 2M L-lysine or $MgCl_2$. Poliovirus ($8\times10^8$ PFU) was added to 1 ml of 5 mM phosphate buffer, pH 7.5, alone (▲) or containing 1M L-lysine (■), 2M L-lysine (□), 1M $MgCl_2$ (●) or 2M $MgCl_2$ (○). The resulting solution was placed in 1.4 ml Eppendorf tubes, sealed and submerged in a water bath at 50° C. Aliquots were removed periodically, diluted with PBS, and the titer of infectious poliovirus was followed by plaque assay on HeLa cells.

We used 0.1 to 2M lysine concentrations to optimize PV1M stability. These data show that 0.3M L-lysine or below provide little extra stability, and that at 2M lysine, poliovirus stability is maximal. FIG. 2 compares stabilization of PVIM by 1 and 2M L-lysine and $MgCl_2$ at pH 7.0. These data show that L-lysine is 10 and 20 times better than $MgCl_2$ at stabilizing PVIM after 24 and 48 hours, respectively, at 50° C.

In another experiment, we sought to determine if stabilization of PV1M by lysine was stereospecific. To do this, we tested L- and D-lysine at 1M concentrations. These data demonstrate that both L- and L-lysine are equally effective in stabilizing PV1M against heat inactivation at 50° C. (Table 1).

TABLE 1

The effect of 1 M L- and D-lysine stereosomers on the stabilization of poliovirus (serotype 1, Mahoney strain) against heat inactivation[a].

| Time (hours at 50 °C.) | Plaque Forming Units Remaining[b] L-lysine | D-lysine | $MgCl_2$ |
|---|---|---|---|
| 0 | 3.7 | 5.9 | 4.1 |
| 3 | 2.1 | 3.1 | 0.61 |
| 6 | 0.93 | 0.82 | 0.44 |
| 12 | 0.65 | 0.49 | 0.28 |
| 20 | 0.13 | 0.09 | 0.06 |
| 24 | 0.11 | 0.05 | 0.04 |

[a]Poliovirus (approximately 4 × $10^8$ PFU) was added to 1 ml of 5 mM phosphate buffer, pH 7.0 containing 1 M of the above compounds. The resulting solutions were placed in 1.4 ml Eppendorf tubes, sealed and submerged in a water bath at 50°C. Aliquots were removed periodically, diluted with PBS and the titer of infectious poliovirus was followed by plaque assay on HeLa cells.
[b]Values should be multiplied by $10^8$ Since lysine has an α- and ε-amino group which may be involved simultaneously in binding opposite charges on the capsid surface, we tested the effect of α- or ε-acetylated derivatives of L-lysine which lack the corresponding α- or ε- $NH_2$ group. In addition, we tested the effect of the carboxyl group of L-lysine by using L-lysine methyl ester. These data demonstrate that L-lysine or its methyl ester were equally protective against heat inactivation, whereas removal of either the α- or ε-$NH_2$ group from L-lysine abrogated the ability of these compounds to stabilize PV1M (Table 2).

TABLE 2

The effect of lysine modification on the stabilization of poliovirus (serotype 1, Mahoney strain) against heat inactivation[a].

| Time (hours at 50° C.) | Plaque Forming Units Remaining[b] N-ε-acetyl-L-lysine | N-α-acetyl-L-lysine | L-lysine methyl ester | lysine |
|---|---|---|---|---|
| 0 | 2.2 | 3.1 | 4.1 | 3.7 |
| 3 | 0.0005 | — | 1.1 | 2.1 |
| 6 | 0.00005 | — | 0.85 | 0.93 |
| 12 | —[c] | — | 0.5 | 0.65 |
| 20 | — | — | 0.2 | 0.13 |
| 24 | — | — | 0.11 | 0.11 |

[a]Poliovirus (approximately 4 × $10^8$ PFU) was added to 1 ml of 5 mM phosphate buffer, pH 7.0 containing 1 M of the above compounds. The resulting solutions were placed in 1.4 ml Eppendorf tubes, sealed and submerged in a water bath at 50° C. Aliquots were removed periodically, diluted with PBS and the titer of infectious poliovirus was followed by plaque assay on HeLa cells.
[b]Values should be multiplied by $10^8$.
[c]Values are below 100 PFU/ml.

These data suggested that compounds other than lysine which contain 2 amino groups might be effective stabilizers.

Consequently, we tested ethylenediamine, poly(ethylenimine), spermidine, 1–5 diaminopentane or ethylamine (a monoamine) at 1M concentration. These data show that ethylenediamine, 1–5 diaminopentane, poly(ethylenimine) are as effective, and spermidine is slightly less effective, than lysine at stabilizing PVIM, whereas ethylamine does not stabilize PV1M (Table 3).

TABLE 3

The effect of mono-, and polyamines and polyimines on the stabilization of poliovirus (serotype 1, Mahoney strain) against heat inactivation[a].

| Time (hours at 50° C.) | Plaque Forming Units Remaining[b] ethylene-diamine | poly (ethylen-imine) | ethyl-amine | sperm-idine | lysine | 1,5-diamino-pentane |
|---|---|---|---|---|---|---|
| 0 | 5.2 | 2.3 | 3.9 | 4.1 | 3.7 | 4.3 |
| 3 | 2.2 | 2.6 | —[c] | 0.19 | 2.1 | 1.4 |
| 6 | 0.6 | 1.7 | — | 0.25 | 0.93 | 1.5 |
| 12 | 0.75 | 0.72 | — | 0.19 | 0.65 | 0.79 |
| 20 | 0.2 | 0.14 | — | 0.041 | 0.13 | 0.25 |
| 24 | 0.19 | 0.07 | — | 0.034 | 0.11 | 0.13 |

[a]Poliovirus (approximately 4 × $10^8$ PFU) was added to 1 ml of 5 mM phosphate buffer, pH 7.0 containing 1 M of the above compounds. The resulting solutions were placed in 1.4 ml Eppendorf tubes, sealed and submerged in a water bath at 50° C. Aliquots were removed periodically, diluted with PBS and the titer of infectious poliovirus was followed by plaque assay on HeLa cells.
[b]Values should be multiplied by $10^8$.
[c]Values are below 100 PFU/ml.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A non-lyophilized stabilized vaccine composition, consisting essentially of:

a) a physiologically acceptable aqueous solution;

b) a poliovirus; and c) a stabilizer which is selected from the group consisting of:

1) lysine;
2) arginine; and
3) a combination of lysine and arginine, said stabilizer being present in the vaccine composition at a concentration sufficient to stabilize the poliovirus against heat inactivation.

2. A vaccine composition of claim 1, wherein the poliovirus is attenuated.

3. A vaccine composition of claim 1, wherein the poliovirus comprises all three types I, II and III.

4. A stabilized vaccine composition, consisting essentially of:

a) a physiologically acceptable aqueous solution;

b) a poliovirus; and c) a stabilizer which is at least one compound comprising two nitrogen-containing groups separated by a spacer moiety which is a substituted or unsubstituted linear chain of 1 to 10 carbon atoms, said stabilizer being present in the vaccine composition at a concentration of about 1–2 molar.

5. A vaccine composition of claim 4, wherein the substituted linear chain of carbon atoms contains nitrogen.

6. A stabilized vaccine composition, comprising:

a) a physiologically acceptable aqueous solution;

b) a poliovirus; and c) a stabilizer consisting essentially of at least one compound selected from the group consisting of:
1) diaminoethane;
2) diaminopropane;
3) diaminobutane;
4) diaminopentane; and
5) spermidine, said stabilizer being present in the vaccine composition at a concentration sufficient to stabilize the virus against heat inactivation.

7. A vaccine composition of claim 6 further comprising magnesium chloride.

8. A vaccine composition of claim 6 wherein the concentration of the stabilizer is about 1–2 molar.

9. A stabilized vaccine composition, comprising:

a) a physiologically acceptable aqueous solution;

b) a poliovirus; and c) a stabilizer consisting essentially of poly(ethylenimine), said stabilizer being present in the vaccine composition at a concentration sufficient to stabilize the virus against heat inactivation.

10. A vaccine composition of claim 9 further comprising magnesium chloride.

11. A vaccine composition of claim 9 wherein the concentration of the stabilizer is about 1–2 molar.

12. A stabilized vaccine composition, consisting essentially of:

a) physiologically acceptable aqueous solution;

b) poliovirus; and c) a stabilizer which is at least one compound selected from the group consisting of:
1) lysine;
2) arginine; and
3) a combination of lysine and arginine, said stabilizer being present in the vaccine composition at a concentration of about 1–2 molar.

13. A non-lyophilized stabilized vaccine composition, consisting essentially of:

a) a physiologically acceptable aqueous solution;

b) a poliovirus; and c) a stabilizer which is magnesium chloride and one compound selected from the group consisting of:
1) lysine;
2) arginine; and
3) a combination of lysine and arginine, said stabilizer being present in the vaccine composition at a concentration sufficient to stabilize the poliovirus against heat inactivation.

14. A vaccine composition of claim 13, wherein the concentration of magnesium chloride is approximately 1 molar.

15. A method of preparing a non-lyophilized stabilized vaccine composition, comprising combining a physiologically acceptable aqueous solution, a poliovirus, and a stabilizer selected from the group consisting of:

a) lysine;

b) arginine; and c) a combination of lysine and arginine, said stabilizer being included in the vaccine composition at a concentration sufficient to stabilize the poliovirus against heat inactivation.

16. The method of claim 15 further comprising combining magnesium chloride with the physiologically acceptable aqueous solution, poliovirus, and stabilizer.

17. A method of preparing a stabilized vaccine composition, comprising combining a physiologically acceptable aqueous solution, a poliovirus, and a stabilizer which is at least one compound selected from the group consisting of:

a) lysine;

b) arginine; and c) a combination of lysine and arginine, wherein the resulting concentration of the stabilizer is about 1–2 molar.

18. A stabilized vaccine composition, comprising:

a) a non-lyophilized trivalent Sabin vaccine; and b) a stabilizer consisting essentially of at least one compound selected from the group consisting of:
1) lysine;
2) arginine; and
3) a combination of lysine and arginine, said stabilizer being present in the vaccine composition at a concentration sufficient to stabilize the virus against heat inactivation.

19. A stabilized vaccine composition, comprising:

a) a non-lyophilized trivalent Sabin vaccine; and b) a stabilizer consisting essentially of magnesium chloride and at least one compound selected from the group consisting of:
1) lysine;
2) arginine; and
3) a combination of lysine and arginine, said stabilizer being present in the vaccine composition at a concentration sufficient to stabilize the virus against heat inactivation.

20. A method of preparing a stabilized vaccine composition, comprising combining a non-lyophilized trivalent Sabin vaccine and a stabilizer consisting essentially of at least one compound selected from the group consisting of:

a) lysine;

b) arginine; and c) a combination of lysine and arginine, said stabilizer being included in the vaccine composition at a concentration sufficient to stabilize the virus against heat inactivation.

21. A method of preparing a stabilized vaccine composition, comprising combining a non-lyophilized trivalent Sabin vaccine and a stabilizer consisting essentially of magnesium chloride and at least one compound selected from the group consisting of:

a) lysine;

b) arginine; and c) a combination of lysine and arginine, said stabilizer being included in the vaccine composition at a concentration sufficient to stabilize the virus against heat inactivation.

22. A method of preparing a stabilized vaccine composition, comprising combining a physiologically acceptable aqueous solution, a poliovirus, and a stabilizer consisting essentially of at least one compound selected from the group consisting of:

a) diaminoethane;

b) diaminopropane;

c) diaminobutane;

d) diaminopentane; and e) spermidine, said stabilizer being included in the vaccine composition at a concentration sufficient to stabilize the virus against heat inactivation.

23. The method of claim 22 further comprising combining magnesium chloride with the physiologically acceptable aqueous solution, poliovirus, and stabilizer.

24. The method of claim 22 wherein the resulting concentration of the stabilizer is about 1–2 molar.

25. A method of preparing a stabilized vaccine composition, comprising combining a physiologically acceptable aqueous solution, a poliovirus, and a stabilizer consisting essentially of poly(ethylenimine), wherein the stabilizer is included in the vaccine composition at a concentration sufficient to stabilize the virus against heat inactivation.

26. The method of claim 25 further comprising combining magnesium chloride with the physiologically acceptable aqueous solution, poliovirus, and stabilizer.

27. The method of claim 25, wherein the resulting concentration of the stabilizer is about 1–2 molar.

28. A stabilized vaccine composition, consisting essentially of:

a) a physiologically acceptable aqueous solution;

b) a poliovirus; and c) a stabilizer which is a basic amino acid, said stabilizer being present in the vaccine composition at a concentration of about 1–2 molar.

29. A stabilized vaccine composition, comprising:

a) a trivalent Sabin vaccine; and b) a stabilizer consisting essentially of at least one compound selected from the group consisting of:
1) lysine;
2) arginine; and
3) a combination of lysine and arginine, said stabilizer being present in the vaccine composition at a concentration of about 1–2 molar.

30. A stabilized vaccine composition, comprising:

a) a trivalent Sabin vaccine; and b) a stabilizer consisting essentially of magnesium chloride and at least one compound selected from the group consisting of:
1) lysine;
2) arginine; and
3) a combination of lysine and arginine, said stabilizer being present in the vaccine composition at a concentration of about 1–2 molar.

31. A method of preparing a stabilized vaccine composition, comprising combining a trivalent Sabin vaccine and a stabilizer consisting essentially of at least one compound selected from the group consisting of:

a) lysine;

b) arginine; and c) a combination of lysine and arginine, said stabilizer being included in the vaccine composition at a concentration of about 1–2 molar.

32. A method of preparing a stabilized vaccine composition, comprising combining a trivalent Sabin vaccine and a stabilizer consisting essentially of magnesium chloride and at least one compound selected from the group consisting of:

a) lysine;

b) arginine; and c) a combination of lysine and arginine, said stabilizer being included in the vaccine composition at a concentration of about 1–2 molar.

* * * * *